United States Patent [19]
Reader

[11] Patent Number: 6,075,059
[45] Date of Patent: Jun. 13, 2000

[54] COMPOSITIONS FOR DENTAL ANESTHESIA

[75] Inventor: Al Reader, Pataskala, Ohio

[73] Assignee: The Ohio State University, Columbus, Ohio

[21] Appl. No.: 09/256,905

[22] Filed: Feb. 24, 1999

[51] Int. Cl.[7] .................................................. A61K 31/045
[52] U.S. Cl. .......................... 514/738; 514/729; 514/309; 514/330; 514/331; 514/447; 514/537; 514/620; 514/626; 514/818
[58] Field of Search ..................................... 514/729, 738, 514/330, 309, 537, 620, 626, 818, 331, 447

[56] References Cited

PUBLICATIONS

"Perineurial Defect and Peripheral Opioid Analgesia in Inflammation" by Antonijevic, et al., *The Journal of Neuroscience*, Jan. 1995, 15(1): 165–171.

"Comparison of Neural Blockade and Pharmacokinetics after Busarachnoid Lidocaine in the Rhesus Monkey. II: Effects of Volume, Osmolality, and Baricity" by Denson, et al., *Anesth Anlg*, 1983;62: 995–1001.

"Osmotic Opening of Perineurial Diffusion Barrier in Peripheral Nerve" by Kristensson, et al., *Neuropathology and Applied Neurobiology*, 1976, 2, 479–488.

Chapter 11 "Neuroanatomical correlates" *Local Anesthetics* by Rudolph H. de Jong, Mosby, St. Louis, Baltimore, Boston, Chicago, London, Madrid, Philadelphia, Sydney, Toronto., 1994.

"Anesthetic efficacy and heart rate effects of the supplemental intraosseous injection of 2% mepivacaine with 1:20,000 levonordefrin" by Guglielmo, et al., *Oral Surgery, Oral Medicine, Oral Pathology*, vol. 87, No. 3, Mar. 1999, pp. 841–293.

"Anesthetic efficacy of the intraosseous injection of 0.9 mL of 2% lidocaine (1:100,000 epinephrine) to augment an inferior alveolar nerve block" by Reitz, et al., *Oral Surgery, Oral Medicine, Oral Pathology*, 1998; 86:516–523.

"Anesthetic efficacy of the supplemental intraosseous injection of 3% mepivacaine in irreversible pulpitis" by Reisman, et al., *Oral Surgery, Oral Medicine, Oral Pathology*, vol. 84, No. 6, Dec. 1997, pp. 676–682.

"Anesthetic Efficacy of the Supplemental Intraosseous Injection of 2% Lidocaine with 1:100,000 Epinephrine in Irreversible Pulpitis" by Nusstein, et al., *Journal of Endodontics*, vol. 24, No. 7, Jul. 1998, pp. 487–491.

"Anestetic Efficacy of the Intraosseous Injection after an Inferior Alveolar Nerve Block" by Dunbar, et al., *Journal of Endodontics*, vol. 22, No. 9, Sep. 1996, pp. 481–486.

Thesis: "The Anesthetic Efficacy of a Combination of 2% Lidocaine with Epinephrine and Mannitol in Human Inferior Alveolar Nerve Block" by Mark Stephen Palo, B.A., D.D.S., Thesis, The Ohio State University, Cataloged on Feb. 25, 1998.

Thesis: "The Anesthetic Efficacy of a Combination of 2% Lidocaine with 1:100,000 Epinephrine and 0.5 Molar Mannitol in Human Inferoir Alveolar Nerve Block" by Ronald Michael Wolf, D.D.S., M.S., The Ohio State University, Cataloged on Oct. 15, 1998.

*Primary Examiner*—Rebecca Cook
*Attorney, Agent, or Firm*—Calfee, Halter & Griswold LLP

[57] ABSTRACT

Anesthetic compositions that achieve enhanced anesthesia of the peripheral nerves located in the mouth region of a subject or patient are provided. Such anesthetic compositions comprise water, a local anesthetic agent, and a sugar alcohol at a concentration of at least 0.1 moles/L i.e., at least 0.1 M. A method of anesthetizing a peripheral nerve of the mouth region is also provided. The method comprises: providing an anesthetic composition comprising water, a local anesthetic agent, and a sugar or, preferably, a sugar alcohol at a concentration of at least 0.1 M; and administering said anesthetic composition to a site proximate to said peripheral nerve.

21 Claims, 4 Drawing Sheets

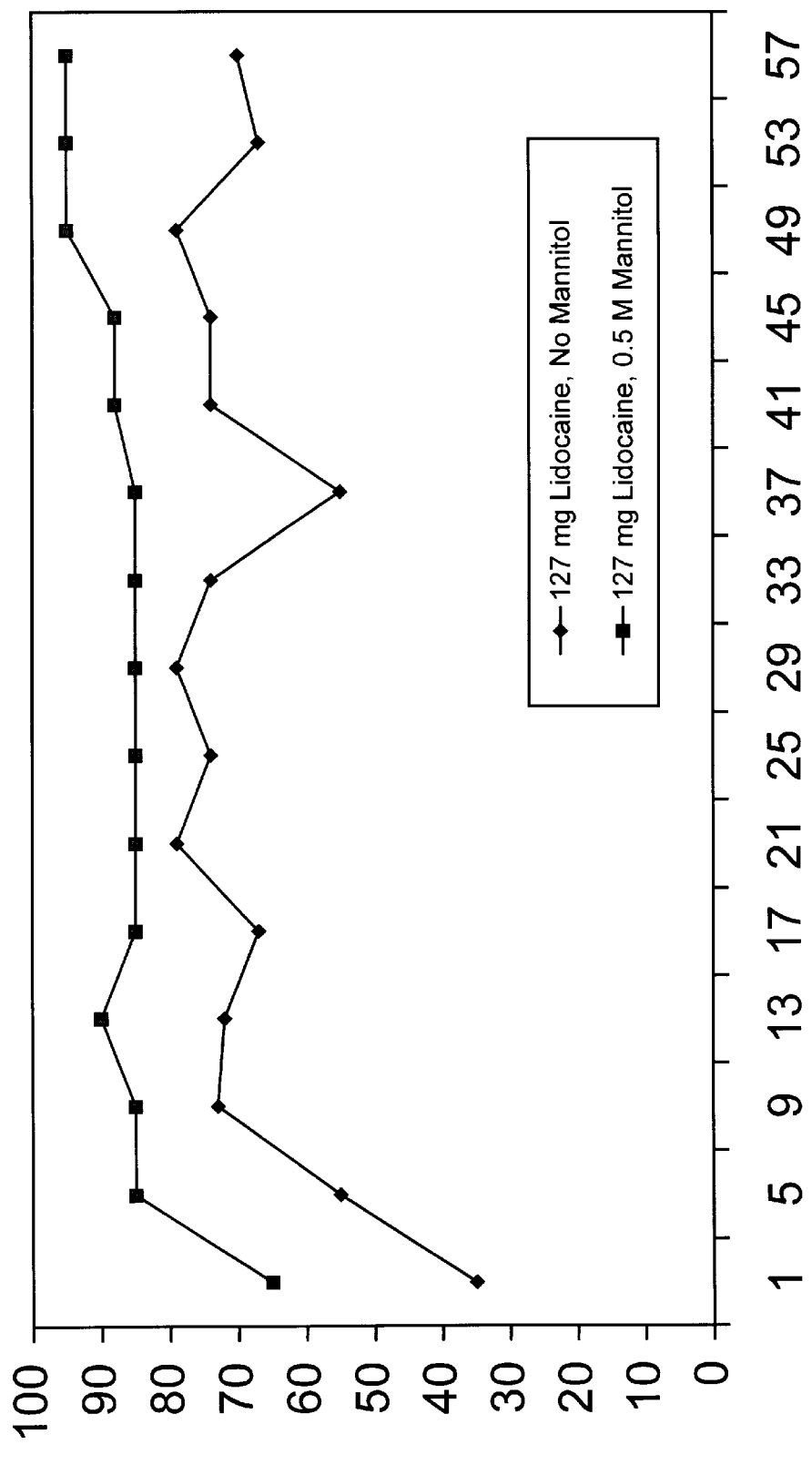

COMPOSITIONS FOR DENTAL ANESTHESIA

BACKGROUND OF THE INVENTION

Local anesthetic agents are used to anesthetize peripheral nerves during many surgical procedures, such as for example during dental surgery. However, profound anesthesia is not always achieved and patients may experience pain during surgical manipulation of the tissue innervated by the incompletely anesthetized nerve. For example, success rates of from only 21% to 67% have been reported when local anesthetic agents have been used to block the inferior alveolar nerve, i.e., the primary nerve of the lower jaw, and its terminal branches. If the area undergoing surgical manipulation is inflamed or if the patient presents with pain, the success rate for profound anesthesia using current techniques and anesthetic compositions is even less.

In recent years studies have been conducted to determine whether increasing the concentration of the local anesthetic agent in the anesthetic composition, increasing the volume of the anesthetic composition administered to the target site, or adding sodium bicarbonate, hyaluronidase, or benadryl to conventional local anesthetic compositions increases the success rate of local anesthesia in the mouth region. Unfortunately, none of these modifications had a significant effect on the anesthetic success rate.

Accordingly, it is desirable to have new anesthetic compositions which are more effective at inhibiting the excitation-conduction process of peripheral nerves, particularly the peripheral nerves the mouth region. New and improved methods for anesthetizing the peripheral nerves of the mouth region are also desirable.

SUMMARY OF THE INVENTION

The present invention is directed to new anesthetic compositions that achieve enhanced anesthesia of the peripheral nerves located in the mouth region of a subject or patient. Such anesthetic compositions comprise water, a local anesthetic agent, and a sugar alcohol at a concentration of at least 0.1 moles/L, i.e., at least 0.1 M.

The present invention is also related to a method of anesthetizing a peripheral nerve of the mouth region. The method comprises: providing an anesthetic composition comprising water, a local anesthetic agent, and a sugar or, preferably, a sugar alcohol at a concentration of at least 0.1 M, and administering said anesthetic composition to a site proximate to said peripheral nerve.

BRIEF DESCRIPTION OF THE DRAWINGS

FIG. 4 is a graph showing percentage of anesthetic success versus time after injection of 3.2 ml of an aqueous solution containing 127 mg lidocaine, 0.032 mg epinephrine and 0.5 M mannitol (open squares), and 3.2 ml of an aqueous solution containing 127 mg lidocaine, 0.032 mg epinephrine without mannitol (closed squares).

DETAILED DESCRIPTION OF THE INVENTION

Figure 1:
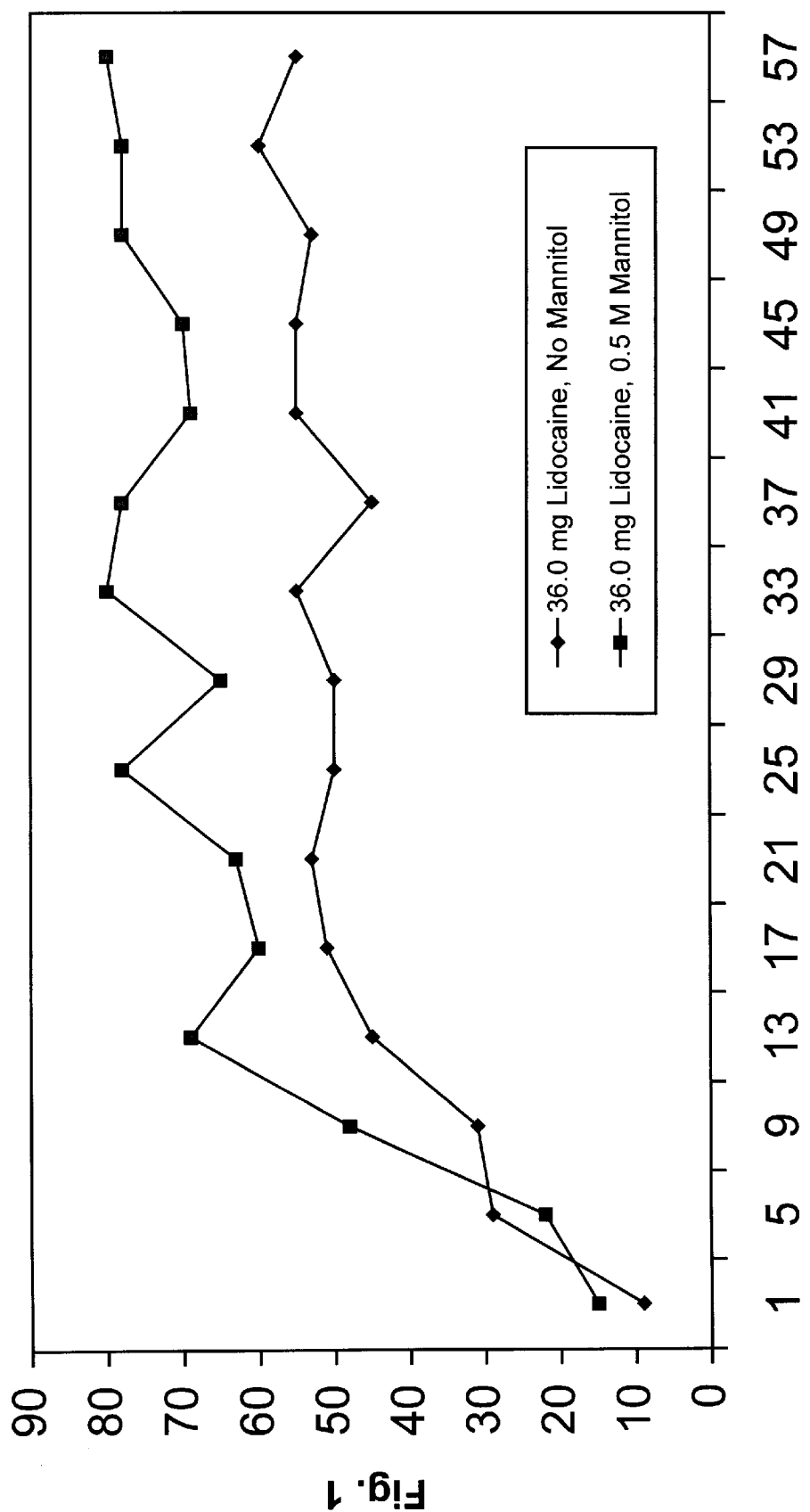
FIG. 1 is a graph showing percentage of anesthetic success versus time after injection of 2.84 ml of an aqueous solution containing 36 mg lidocaine, 0.018 mg epinephrine and 0.5 M mannitol (open squares), and 1.8 ml of an aqueous solution containing 36 mg lidocaine, 0.018 mg epinephrine without mannitol (closed squares).

The present invention provides anesthetic compositions for enhanced local anesthesia of the peripheral nerves of the mouth region. The present invention also provides an improved method for anesthetizing peripheral nerves of the mouth region.

Anesthetic Compositions

Upon administration, the anesthetic compositions of the present invention comprise water, a local anesthetic agent, and a sugar alcohol at a concentration of at least 0.1 M. Preferably, the anesthetic compositions have a pH of from about 3 to about 7.9, more preferably from about 3.5 to about 6.5.

A "local anesthetic agent", as used herein refers to a clinically acceptable, non-narcotic drug which inhibits the excitation of a peripheral nerve or the conduction of an electrical impulse along the peripheral nerve, thereby causing localized numbness or prevention of sensation to painful stimuli in the region innervated by the relevant peripheral nerve. Preferably, the local anesthetic agent is composed of an aromatic nucleus ($R_1$) connected by an ester or an amide linkage to an aliphatic chain containing a secondary or a tertiary amino group as illustrated below:

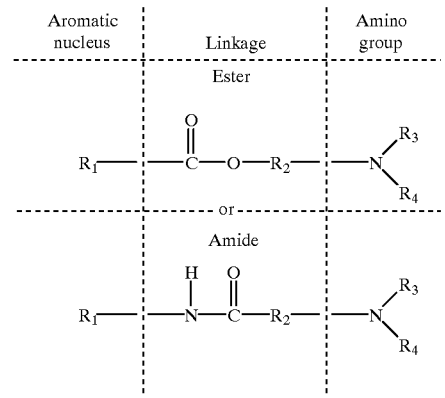

Examples of suitable local anesthetic agents are lidocaine, xylocaine, mepivacaine, prilocaine, chloroprocaine, procaine, propoxycaine, dibucaine, bupivacaine, etidocaine, ropivacaine, and articaine. Such anesthetic agents are free bases which form water-soluble salts with acids. For preparation of an injectable aqueous anesthetic composition, it is preferred that the local anesthetic agent be in the form of a salt such as, for example, a hydrochloride salt or a hydrocarbonate salt of the local anesthetic agent. Aqueous solutions of the salt forms of local anesthetic agents are available commercially. Preferably, the concentration of the local anesthetic agent in the anesthetic composition is from about 20 mg/ml to about 500 mg/ml more preferably from about 36 mg/ml to about 300 mg/ml most preferably from about 70 mg/ml to about 160 mg/ml.

The sugar alcohols of the anesthetic composition have from about 4 to about 6 carbon atoms. Suitable sugar alcohols are, by way of example, erythritol, inositol, perseitol, ribitol, xylitol, sorbitol, galactitol, or, preferably, mannitol. The concentration of the sugar alcohol in the anesthetic composition is at least 0.1 M. Preferably, the concentration of the sugar alcohol in the final anesthetic composition is from 0.1 M to saturated, more preferably from about 0.3 M to about 3.0 M. most preferably from about 0.5 to about 0.9 M.

Preferably, the anesthetic composition further comprises vasoconstrictors to decrease blood flow at the site of injection, The result of such decreased blood flow is a decrease in toxicity and prolongation of the duration of anesthesia. Examples of suitable vasoconstrictors are epinephrine, norepinephrine, levonordefrin, phenylephrine, and felypressin.

Preferably, the concentration of the vasoconstrictor in the anesthetic composition is from about 0.005 mg/ml to about 0.04 mg/ml. Optionally, the anesthetic composition contains an antibacterial agent; an antifungal agent; a preservative such as methylparaben; preservatives for the vasoconstrictor agents such as sodium bisulfite or metabisulfite; diluents, or combinations thereof.

Methods for Anesthetizing Peripheral Nerves of the Mouth Region

The present invention also provides a method for anesthetizing a peripheral nerve of the mouth region. In general, a nerve is composed of parallel axons running together in bundles and ensheathed in a dense fibrous sleeve. The method comprises: providing an aqueous anesthetic composition comprising a local anesthetic agent and a sugar or, preferably, a sugar alcohol at a final concentration of at least 0.1 M; and administering the anesthetic composition to a site external to the dense fibrous sleeve ensheathing the peripheral nerve. Such method is particularly useful during procedures such as, for example, restorative or operative dentistry, which involve preparing and filling cavities; prosthodonitic dentistry which involves preparing and fitting crowns on teeth; oral surgery on soft and hard tissues of the upper and lower jaws and contiguous structures; endodontia; periodontal surgery which involves gingival and bone work around the teeth; and implant procedures which involve placement of artificial teeth into the lower and upper jaws.

Suitable sugar alcohols are, by way of example, erythritol, inositol, perseitol, ribitol xylitol, sorbitol, galactitol, or, preferably, mannitol. Suitable sugars are, by way of example, monosaccharides, such glucose, erythrose, mannose, and galactose, fructose, threose, and ribose; disaccharides such as sucrose, lactose, cellobiose, and maltose, and polysaccharides such as dextran and glycogen. The concentration of the sugar or the sugar alcohol in the anesthetic composition is at least 0.1 M. Preferably, the concentration of the sugar or sugar alcohol in the anesthetic composition is 0.1 M to saturated, more preferably from about 0.3 M to about 3.0 M, most preferably from about 0.5 to about 0.9 M.

Preferably the anesthetic composition is administered by injection to a site proximate to the peripheral nerve using conventional techniques. Preferably, a single injection is used. If the first injection does not result in anesthesia of the soft tissues of the lip or adjacent soft tissue proximate to the site of injection, a second dose is typically administered.

The amount of local anesthetic agent administered per injection is preferably from about 0.9 mg to about 160 mg, more preferably from about 36 mg to about 160 mg. The volume of the anesthetic composition that is administered in the first injection is preferably from about 2 ml to about 5 ml and depends upon the concentration of the anesthetic agent in the anesthetic composition and the anatomical boundaries of the injection site.

Conventional techniques for administering anesthetics are used. For anesthetizing the lower jaw and the pulpal tissue of the teeth in the lower jaw and the soft tissue of the lower jaw, the preferred procedure is an inferior alveolar nerve block, a conventional technique which involves injection of the anesthetic composition into the pterygomandibular space and proximate to the inferior alveolar nerve. Alternatively, a Gow-Gates nerve block or a Vaziarani-Akinosi nerve block is used to anesthetize the lower jaw and the pulp region of the lower jaw and the pulpal tissue of the teeth in the lower jaw and the soft tissue of the lower jaw. In these latter procedures the anesthetic composition is injected into the pterygomandibular space and proximate to the inferior alveolar nerve. Another conventional technique for numbing the premolar and anterior teeth in the lower jaw is the incisive nerve block, in which the anesthetic composition is injected into the mental foramen, i.e., the natural opening in the lower jaw between the premolar teeth. Alternatively, a particular tooth in the lower jaw is numbed by injecting the anesthetic composition under the alveolar mucosa next to such tooth.

For numbing the teeth in the upper jaw, the preferred method of administration is the infiltration injection, in which the anesthetic composition is injected under the alveolar mucosa next to the targeted tooth. Following injection, the anesthetic composition diffuses through the bone to reach the nerves around the targeted tooth. Alternatively, the upper molar teeth are numbed using a posterior superior alveolar nerve block, a conventional technique in which the anesthetic composition is injected into the alveolar mucosa behind the last tipper tooth. An alternative procedure for numbing the upper premolar teeth is the middle superior alveolar nerve block, a conventional technique in which the anesthetic composition is injected under the alveolar mucosa next to the premolar teeth. Alternative procedures for numbing the upper anterior teeth is the anterior superior alveolar nerve block. To anesthetize the anterior superior alveolar nerve, the anesthetic composition is either injected under the alveolar mucosa above the premolar teeth or just below the eye and into the infraorbital foramen which contains the anterior superior alveolar nerve.

Additional techniques for numbing particular teeth in the lower and upper jaws include the periodontal ligament injection, in which the anesthetic composition is injected into the gingival sulcus next to the tooth and the intraosseous injection where the anesthetic composition is injected into the cancellous bone in the inside of the mandible.

The present invention is further described by the following non-limiting examples which are not intended in any way to limit the scope of the invention.

EXAMPLE 1

An anesthetic composition comprising lidocaine, epinephrine and mannitol at a final concentration of 0.5 M was prepared by mixing the contents of a solution containing 2% lidocaine with 1:100,000 epinephrine obtained from Astra Pharmaceutical Products, Inc., Westborough, and an aqueous solution containing 1.373 M mannitol obtained from American Reagent Laboratories, Inc., Shirley, N.Y. To dissolve any crystals that were present, the mannitol solution was heated at 80° C. for a period of 15 minutes before being added to the syringe containing the lidocaine solution.

The efficacy of the anesthetic composition was assessed in forty adult human subjects. All the subjects were in good physical condition as determined by a written health questionnaire and oral questioning. Subjects taking medications that would alter pain perception were excluded. Also excluded were subjects who had contraindications to the injection technique, to the anesthetic solution (2% lidocaine with 1:100,000 epinephrine) or to an aqueous solution containing 0.5 M mannitol.

Subjects were tested at three successive appointments spaced at least one week apart.

Each subject received the following three solutions: (1) 2.84 ml of an aqueous solution containing 36 mg lidocaine, 0.018 mg epinephrine and 0.5 M mannitol, (2) 5 ml of an aqueous solution containing 63.4 mg lidocaine, 0.032 mg epinephrine and 0.5 M mannitol; and (3) 1.8 ml of an aqueous solution containing 36 mg lidocaine, 0.018 mg epinephrine without mannitol. The solutions were administered separately to each subject in a predetermined, random sequence.

The conventional inferior alveolar injection technique as described by Malamed in Handbook of Local Anesthesia, 4th edition, C. V. Mosby, St. Louis., Mo., 1997. was used to administer the solutions. The injection site was the soft tissue overlying the medial surface of the ramus, lateral to the pterygomandibular raphe, at a height determined by the coronoid notch on the anterior border of the ramus. With the subject's mouth wide open, the thumb of the noninjecting hand was placed over the pterygomandibular triangle and then pulled laterally until the deepest depression in the anterior border of the ramus was felt. The first or second finger of the noninjecting hand palpated the posterior portion of the ramus, finding a slight depression. The line between the thumb and the finger established the vertical height of the injection site. The direction of needle insertion was from the contralateral mandibular premolars and directed parallel to the occlusal plane. The needle was advanced over a time period of approximately ten seconds to the target site until bone was gently contacted, a depth of penetration of approximately 16 to 20 millimeters. As the needle was advanced, approximately 0.2 ml of solution was deposited. After contact with bone was made, the needle was withdrawn approximately 1 mm, aspiration performed, and the bolus of anesthetic solution was deposited over a period of one minute. There were no significant differences among the anesthetic solutions with respect to the pain or discomfort the subjects experienced during administration of the three solutions or postoperatively.

To determine the efficacy of each solution, electric pulp testers were used to measure the responsiveness to electrical stimulation of the second and first molars, the second and first premolars, and the lateral and central incisors on the injected side of each subject both before and after injection of the solution. The contralateral canine served as the negative control. Teeth with a history of trauma or sensitivity were eliminated. Teeth with previous endodontic therapy, large restorations, caries, full crowns, periodontal disease, or restorations with poor margins were also eliminated.

The electric pulp testers were obtained from Analytic Technology Corp., Redmond, Wash. The Analytic Technology digital electric pulp tester delivers a cathodal polarity current ouput from 0 to 50 microamperes and generates an output voltage that ranges from 15 to 300 volts. The maximum value shown on the digital readout is 80 and correlates with the maximum voltage and amperage of this pulp tester. Previous studies described by Certosimo and Archer in Oper. Dent. 21:25–30 (1996) have shown that patients who do not feel a sensation at the maximum voltage (80/80 reading) do not experience pain during subsequent dental surgery.

The testing procedure was as follows: the teeth to be tested were isolated with cotton rolls and dried with cotton gauze. A small amount of gel toothpaste was used as the electrolyte between the electrode of the pulp tester and the tooth. The electrode was placed on sound enamel in the middle third of the facial surface of the crown of the tooth. The electrode was not placed on restorations, nor on exposed dentin. The pulp testing commenced upon contact of the electrode to the tooth surface and ended when the subject indicated an initial sensation in the tooth. The value from the digital readout of the electric pulp tester was then recorded. Testing was stopped and a value of 80/80 was recorded if the subject did not feel a sensation at maximum voltage (80 reading).

At each appointment, the test teeth and the control canine were tested three times with the electric pulp tester prior to any injection to obtain baseline response information. Post-injection pulp testing began one minute after the injection. At one minute post-injection, the experimental first and second molars were tested with the electric pulp tester and the results recorded. At two minutes postinjection, the premolars were tested. At three minutes post-injection, the incisors were tested. At four minutes post-injection, the control canine was tested. This cycle of testing was repeated every four minutes. The negative control canine was tested every third cycle with a non-activated wand from a pulp tester in order to test the reliability of the subject. Pulp testing continued for sixty minutes.

Pulpal anesthesia, as used herein means that at some point during the 60 minute testing, the subject did not experience any sensation in the tooth at maximum voltage, i.e., a reading of 80 on the pulp tester. The mean total percent pulpal anesthesia of each tooth tested is shown in Table 1 below.

TABLE 1

| | Mean Percent Total Anesthesia* | |
|---|---|---|
| | Solution | |
| Tooth | (1) | (2) |
| Second Molar | 75 +/− 32 A | 84 +/− 25 B |
| First Molar | 48 +/− 35 A | 64 +/− 32 B |
| Second Premolar | 54 +/− 40 A | 66 +/− 34 B |
| First Premolar | 50 +/− 41 A | 66 +/− 36 B |
| Lateral Incisor | 27 +/− 36 A | 28 +/− 37 A |
| Central Incisor | 12 +/− 25 A | 14 +/− 29 A |

1) 1.8 ml of an aqueous solution containing 36 mg lidocaine, 0.018 mg epinephrine and no mannitol (control);
2) 2.84 ml of an aqueous solution containing 36 mg lidocaine, 0.018 mg epinephrine and 0.5 M mannitol;
Means with same letter are not significantly different (p>0.05) for each tooth.
Means with different letters are significantly different (p>0.05) for each tooth
* Mean total percent pulpal anesthesia for each tooth in all the subjects was assessed using logistic regression. A separate model was used for each tooth. The dependent variable was the binary response of anesthesia status (i.e., anesthesia, 80 reading, or no anesthesia, not 80 reading) and the independent variables were assessment period (time) and solution. The model fit was determined by the scaled deviance and Pearson's chi-square statistics. In each case, the model fit well without the interaction term (time x solution). The generalized estimating equation model was used to control for the correlations among the binary responses for the individual subjects. P-values were multiplied by the number of models used for each tooth (2) and the number of teeth (6) resulting in a total of 12.

As shown in Table 1, pulpal anesthesia was achieved more often with the anesthetic composition of the present invention than with a conventional composition which lacks a sugar alcohol. An even greater increase in pulpal anesthesia occurred with an anesthetic composition containing mannitol and an increased amount of lidocaine, i.e., 63.4 mg.

Anesthesia was considered successful if the tooth, in addition to exhibiting pulpal anesthesia at some point during the one hour testing period, achieved an 80/80 reading within fifteen minutes and continuously sustained this reading for sixty minutes. Anesthetic failure was considered to have occurred if the subject never achieved two consecutive 80/80 readings. The percentages and numbers of subjects who experienced anesthetic success and failure in the mandibular first molar upon receiving an anesthetic composition of the present invention as compared to subjects receiving a conventional composition are presented in Table 2 below.

Table 2. Comparison of Anesthetic Success and Failure in Subjects Receiving an Anesthetic Composition of the Present Invention and a Conventional Anesthetic Composition.

| Tooth | 36 mg Lidocaine No Mannitol | 36 mg Lidocaine 0.5M Mannitol |
|---|---|---|
| Anesthetic Success: | | |
| 1st Molar | 36% (14/39) | 51% (20/39) |
| Anesthetic Failure: | | |
| 1st Molar | 31% (12/39) | 15% (6/39) |

As shown in Table 2 and FIG. 1, the percentage for anesthetic success was greater with the novel anesthetic composition of the present invention than with a conventional composition. The percentage of first molars that never achieved anesthesia was greater with a conventional composition that lacked mannitol as compared to a composition of the present invention that contained mannitol. Thus, anesthetic efficacy is improved with anesthetic compositions containing at least 0.1 M of a sugar alcohol. The percentage for anesthetic success was even greater with the composition containing 0.5 M mannitol and 63.4 mg of mannitol.

EXAMPLE 2

An anesthetic composition containing 22.8 mg lidocaine. 0.011 mg epinephrine and 0.5 M mannitol and a control composition containing 36 mg lidocaine, 0.018 mg epinephrine and no mannitol were administered to 60 subjects via an inferior alveolar nerve block as described above in Example 1. The percentages and numbers of subjects who experienced anesthetic success and failure upon receiving the anesthetic composition and the control composition are presented in Table 3 below.

Table 3 Comparison of Anesthetic Success and Failure in Subjects Receiving an Anesthetic Composition of the Present Invention and a Conventional Anesthetic Composition.

| Tooth | 36 mg Lidocaine No mannitol | 22.8 mg Lidocaine 0.5M mannitol |
|---|---|---|
| Anesthetic Success: | | |
| 1st Molar | 32% (19/60) | 27% (16/60) |
| Anesthetic Failure: | | |
| 1st Molar | 38% (23/60) | 25% (15/60) |

Figure 2:
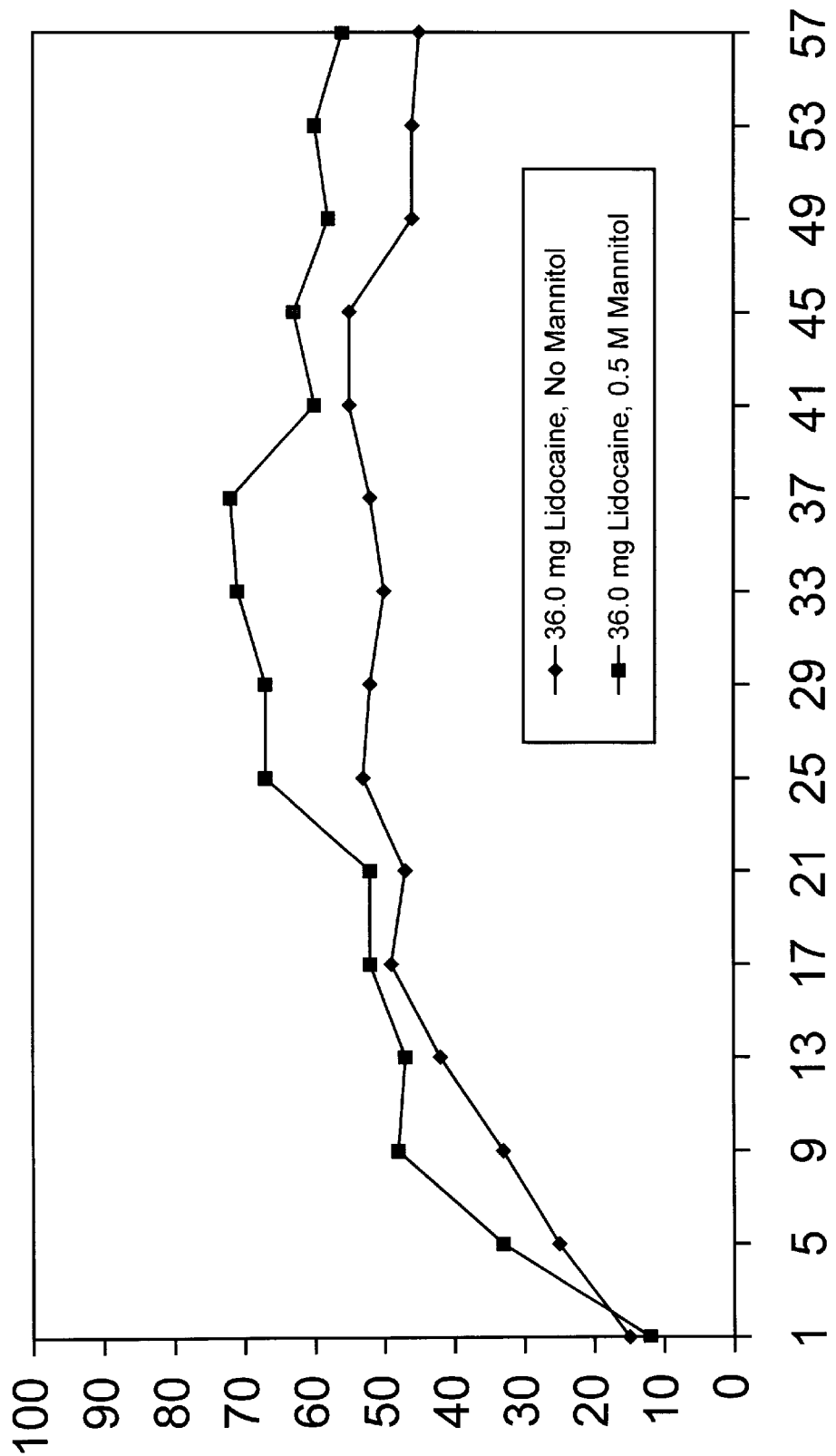
FIG. 2 is a graph showing percentage of anesthetic success versus time after injection of 1.8 ml of an aqueous solution containing 22.8 mg lidocaine, 0.011 mg epinephrine and 0.5 M mannitol (open squares) and 1.8 ml of an aqueous solution containing 36 mg lidocaine, 0.018 mg epinephrine without mannitol (closed squares).

As shown in table 3 and FIG. 2, the percentage of anesthetic success with a composition of the present invention was similar to the percentage of anesthetic success with a conventional composition which lacked mannitol but contained more lidocaine. Thus, an anesthetic composition of the present invention containing less than the standard dose of lidocaine is as effective as a conventional anesthetic composition containing the standard dose. As shown in table 3, the percentages of first molars that never achieved anesthesia was greater for the conventional composition than for an anesthetic composition of the present invention.

EXAMPLE 3

Anesthetic compositions containing lidocaine and 0.75 M or 0.9 M mannitol were administered to 20 subjects via an inferior alveolar block as described above in example. A conventional composition containing lidocaine and lacking mannitol was also administered to the subjects as described in example 1. The compositions were as follows: (1) 3.8 ml of an aqueous solution containing 68.8 mg lidocaine, 0.017 mg epinephrine and 0.75 M mannitol, (2) 5 ml of an aqueous solution containing 68.8 mg lidocaine, 0.017 mg epinephrine and 0.9 M mannitol, and (3) 1.72 ml of an aqueous solution containing 68.8 mg lidocaine, 0.017 mg epinephrine and no mannitol. The anesthetic successes and the anesthetic failures achieved upon administration of each composition were determined as described in example 1. The percentages and numbers of subjects who experienced anesthetic success and failure are presented below in Table 4.

Table 4: Comparison of Anesthetic Success and Failure in Subjects Receiving an Anesthetic Composition of the Present Invention and a Conventional Anesthetic Composition.

| Tooth | 68.8 mg Lidocaine No mannitol | 68.8 mg Lidocaine 0.75M mannitol | 68.8 mg Lidocaine 0.9M Mannitol |
|---|---|---|---|
| Anesthetic Success: | | | |
| 1st Molar | 50% (10/20) | 60% (12/20) | 80% (16/20) |
| Anesthetic Failure: | | | |
| 1st Molar | 20% (4/20) | 15% (3/20) | 10% (2/20) |

Figure 3:
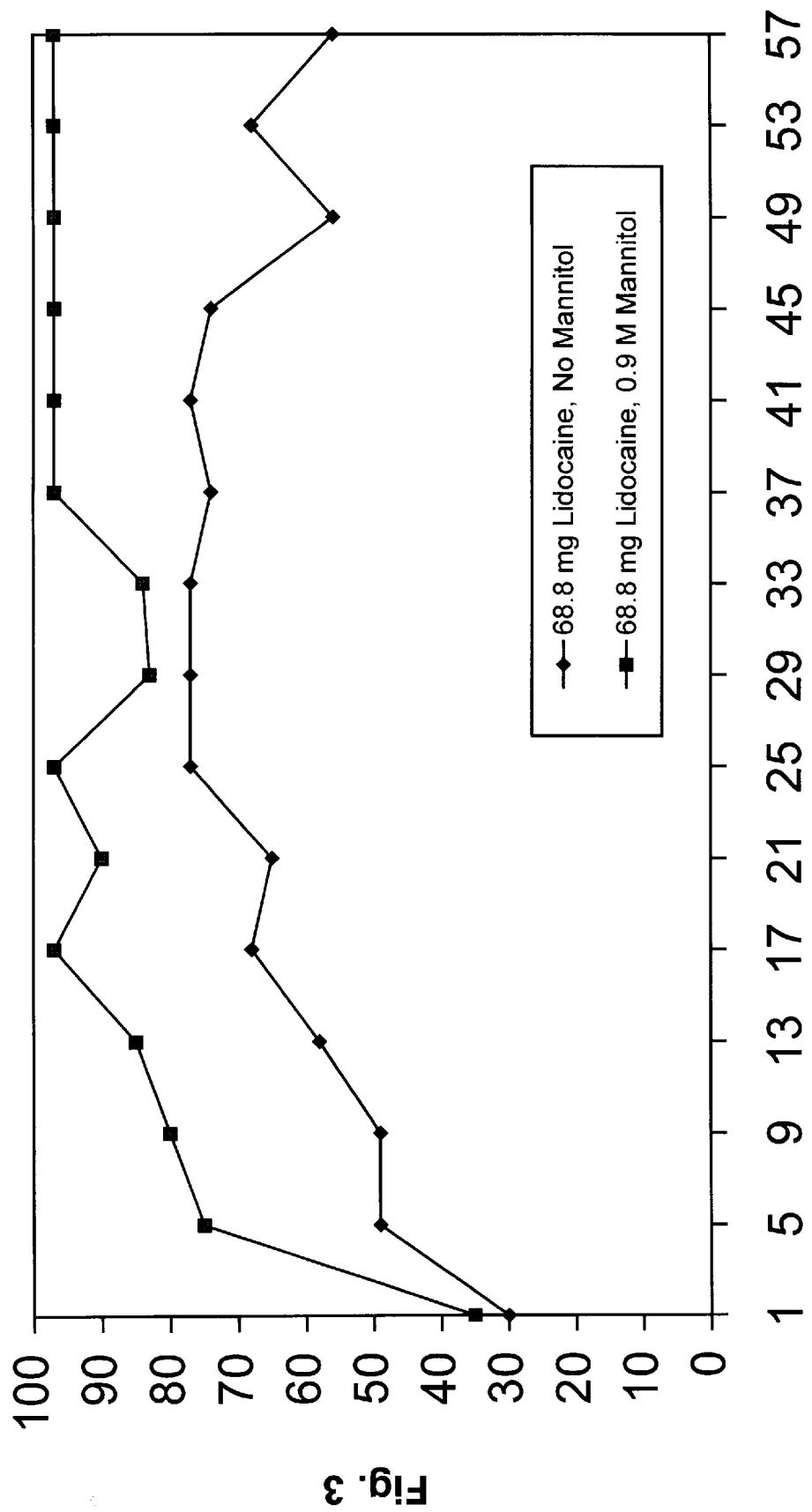
FIG. 3 is a graph showing percentage of anesthetic success versus time after injection of 5 ml of an aqueous solution containing 68.8 mg lidocaine, 0.017 mg epinephrine and 0.9 M mannitol (open triangles), and 1.72 ml of an aqueous solution containing 68.8 mg lidocaine, 0.017 mg epinephrine and no mannitol (closed squares).

As shown in Table 4 and FIG. 3, anesthetic success was greater with the anesthetic composition containing lidocaine and 0.9 M mannitol than with a conventional composition which lacked a sugar alcohol. A greater percentage of anesthetic success was also attained with a composition that contained 0.75 M mannitol. The percentage of first molars that never achieved anesthesia was greater with a conventional composition that lacked a sugar alcohol as compared to either anesthetic composition of the present invention. Thus, the presence of mannitol improves anesthetic efficacy.

EXAMPLE 4

An anesthetic compositions containing lidocaine and 0.5 M mannitol was administered to 20 subjects as described above in example 1. A conventional composition containing lidocaine but lacking mannitol was also administered to the subjects.

The compositions were as follows: (1) 3.2 ml of an aqueous solution containing 127 mg lidocaine, 0.032 mg epinephrine and 0.5 M mannitol; and (2) 3.2 ml of an aqueous solution containing 127 mg lidocaine, 0.032 mg epinephrine without mannitol. The anesthetic successes and the anesthetic failures achieved upon administration of each composition were determined as described in example 1. The percentages and numbers of subjects who experienced anesthetic success and failure are presented below in Table 5.

Table 5 Comparison of Anesthetic Success and Failure in Subjects Receiving an Anesthetic Composition of the Present Invention and a Conventional Anesthetic Composition.

| Tooth | 127 mg Lidocaine No Mannitol | 127 mg Lidocaine 0.5M Mannitol |
|---|---|---|
| Anesthetic Success: | | |
| 1st Molar | 40% (8/20) | 85% (17/20) |
| Anesthetic Failure: | | |
| 1st Molar | 10% (2/20) | 5% (1/20) |

As shown in Table 5 and FIG. 4, anesthetic success was greater with an anesthetic composition of the present invention than with a conventional composition lacking mannitol. As shown in Table 5, the percentage of first molars that never achieved anesthesia was greater with a conventional composition that lacked a sugar alcohol as compared to an anesthetic composition of the present invention.

While the invention has been described to some degree of particularity, various adaptations and modifications can be made without departing from the scope of the invention as defined in the appended claims.

What is claimed is:

1. An anesthetic composition for enhanced anesthesia of peripheral nerves comprising:
   (a) water;
   (b) a local anesthetic agent; and
   (c) a sugar alcohol at a concentration of at least 0.1 M.

2. The composition of claim 1 wherein the concentration of the sugar alcohol is from 0.1 M to saturated.

3. The composition of claim 1 wherein the concentration of the sugar alcohol is from about 0.3 M to about 3.0 M.

4. The composition of claim 1 wherein the concentration of the sugar alcohol is from about 0.5 M to about 0.9 M.

5. The composition of claim 1 wherein the sugar alcohol is selected from the group consisting of erythritol, inositol, perseitol, ribitol xylitol, sorbitol, galactitol, and mannitol, or a combination thereof.

6. The composition of claim 1 wherein the sugar alcohol is mannitol.

7. The composition of claim 1 wherein the local anesthetic agent comprises an aromatic nucleus connected by an ester or an amide linkage to an aliphatic chain comprising a secondary or tertiary amine.

8. The composition of claim 1 wherein said local anesthetic agent is a salt or a free base of a local anesthetic agent selected from the group consisting of lidocaine, mepivacaine, prilocaine, chloroprocaine, procaine, propoxycaine, dibucaine, bupivacaine, ropivacaine, etidocaine, and articaine, or a combination thereof.

9. The anesthetic composition of claim 8 wherein the local anesthetic agent is a hydrocarbonate salt or a hydrochloride salt of said local anesthetic agent.

10. The anesthetic composition of claim 1 further comprising a vasoconstrictor.

11. The anesthetic composition of claim 1 wherein said sugar alcohol is present at a concentration of from 0.1 M to saturated and wherein said sugar alcohol is selected from the group consisting of erythritol, inositol, perseitol, ribitol, xylitol, sorbitol, galactitol, and mannitol, or a combination thereof.

12. The anesthetic composition of claim 1 wherein said sugar alcohol is present at a concentration of from 0.3 M to about 3.0 M and wherein said local anesthetic agent comprises an aromatic nucleus connected by an ester or an amide linkage to an aliphatic chain comprising a secondary or tertiary amine.

13. A method for anesthetizing a peripheral nerve of the mouth region comprising:
   (a) providing an anesthetic composition comprising:
      (i) water
      (ii) a local anesthetic agent, and
      (iii) a sugar or a sugar alcohol at a concentration of at least 01.1 M; and
   (b) administering said anesthetic composition topically or by injection to a site proximate to a peripheral nerve of the mouth region.

14. The method of claim 13 wherein the sugar or sugar alcohol is present at concentration of 0.1 M to saturated.

15. The method of claim 13 wherein the anesthetic composition comprises a sugar alcohol selected from the group consisting of erythritol, inositol, perseitol, ribitol, xylitol, sorbitol, galactitol, and mannitol, or a combination thereof.

16. The method of claim 13 wherein the local anesthetic agent comprises an aromatic nucleus connected by an ester or an amide linkage to an aliphatic chain comprising a secondary or tertiary amine.

17. The method of claim 13 wherein the anesthetic composition comprises a salt or a free base of a local anesthetic agent selected from the group consisting of lidocaine, mepivacaine, prilocaine, chloroprocaine, procaine, propoxycaine, dibucaine, bupivacaine, ropivacaine, etidocaine, and articaine, or a combination thereof.

18. The method of claim 13 wherein the anesthetic composition comprises mannitol.

19. The method of claim 13 wherein the anesthetic composition comprises a sugar alcohol and a local anesthetic which comprises an aromatic nucleus connected by an ester or an amide linkage to an aliphatic chain comprising a secondary or tertiary amine.

20. The method of claim 13 wherein the anesthetic composition is administered to a site proximate to a peripheral nerve selected from the group consisting of the inferior alveolar nerve, the incisive nerve, the anterior superior alveolar nerve, the middle superior alveolar nerve, the posterior superior alveolar nerve, the maxillary nerve, and the nasopalatine nerve.

21. The method of claim 13 wherein the anesthetic composition is administered by injection.

* * * * *

UNITED STATES PATENT AND TRADEMARK OFFICE
CERTIFICATE OF CORRECTION

PATENT NO.    : 6,075,059
DATED         : June 13, 2000
INVENTOR(S)   : Al Reader Page 1 of 1

It is certified that error appears in the above-identified patent and that said Letters Patent is hereby corrected as shown below:

<u>Column 10,</u>
Line 25, please delete "01.1" and insert -- 0.1 --.

Signed and Sealed this

Thirty-first Day of July, 2001

Attest:

*Nicholas P. Godici*

Attesting Officer

NICHOLAS P. GODICI
*Acting Director of the United States Patent and Trademark Office*